United States Patent
Min et al.

(10) Patent No.: US 12,017,078 B2
(45) Date of Patent: *Jun. 25, 2024

(54) ENHANCED IMPLANT-TO-IMPLANT COMMUNICATIONS USING ACCELEROMETER

(71) Applicant: Pacesetter, Inc., Sylmar, CA (US)

(72) Inventors: Xiaoyi Min, Santa Rosa Valley, CA (US); David Ligon, San Francisco, CA (US); Weiqun Yang, Cupertino, CA (US); Shawn Chen, Santa Clarita, CA (US); Matthew G. Fishler, Scotts Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,158

(22) Filed: Mar. 22, 2023

(65) Prior Publication Data

US 2023/0233867 A1 Jul. 27, 2023

Related U.S. Application Data

(63) Continuation of application No. 17/370,210, filed on Jul. 8, 2021, now Pat. No. 11,642,536, which is a
(Continued)

(51) Int. Cl.
*A61N 1/372* (2006.01)
*A61N 1/362* (2006.01)
(Continued)

(52) U.S. Cl.
CPC ..... *A61N 1/37288* (2013.01); *A61N 1/36542* (2013.01); *A61N 1/37217* (2013.01);
(Continued)

(58) Field of Classification Search
CPC ............ A61N 1/37288; A61N 1/36542; A61N 1/37217; A61N 1/37229; A61N 1/37235;
(Continued)

(56) References Cited

U.S. PATENT DOCUMENTS 8,386,049 B2   2/2013   Persson et al.
8,554,333 B2   10/2013  Wu et al.
(Continued)

OTHER PUBLICATIONS

Non-final Office Action dated Feb. 22, 2021, U.S. Appl. No. 16/171,080, filed Oct. 25, 2018.
(Continued)

*Primary Examiner* — Mallika D Fairchild
(74) *Attorney, Agent, or Firm* — Vierra Magen Marcus LLP

(57) ABSTRACT

Embodiments described herein relate to implantable medical devices (IMDs) and methods for use therewith. Such a method includes using an accelerometer of an IMD (e.g., a leadless pacemaker) to produce one or more accelerometer outputs indicative of the orientation of the IMD. The method can also include the IMD using an accelerometer to identify when the orientation of the IMD is such that the IMD will likely be able to successfully communicate with another IMD via one or more communication pulses sent from the IMD to the other IMD. The method also includes the IMD sending of the one or more communication pulses, that are used to communicate with the other IMD, when the orientation of the IMD is such that the IMD will likely be able to successfully communicate with the other IMD via one or more communication pulses sent from the IMD to the other IMD.

24 Claims, 8 Drawing Sheets

Related U.S. Application Data continuation of application No. 16/171,080, filed on Oct. 25, 2018, now Pat. No. 11,090,497.

(60) Provisional application No. 62/731,317, filed on Sep. 14, 2018.

(51) Int. Cl.
*A61N 1/365* (2006.01)
*A61N 1/37* (2006.01)
*A61N 1/375* (2006.01)
*A61N 1/39* (2006.01)
*H04B 13/00* (2006.01)

(52) U.S. Cl.
CPC ..... *A61N 1/37229* (2013.01); *A61N 1/37235* (2013.01); *A61N 1/3756* (2013.01); *A61N 1/39622* (2017.08); *H04B 13/005* (2013.01); *A61N 1/3622* (2013.01); *A61N 1/36514* (2013.01); *A61N 1/3706* (2013.01); *A61N 1/37254* (2017.08); *A61N 1/37276* (2013.01)

(58) Field of Classification Search
CPC .............. A61N 1/3756; A61N 1/39622; A61N 1/3622; A61N 1/36514; A61N 1/3706; A61N 1/37254; A61N 1/37276
See application file for complete search history.

(56) References Cited

U.S. PATENT DOCUMENTS

| | | |
|---|---|---|
| 9,457,193 B2 | 10/2016 | Klimovitch et al. |
| 9,522,280 B2 | 12/2016 | Fishler et al. |
| 9,561,382 B2 | 2/2017 | Persson et al. |
| 11,090,497 B2 | 8/2021 | Min et al. |
| 2006/0161211 A1 | 7/2006 | Thompson et al. |
| 2015/0224320 A1 | 8/2015 | Stahmann |
| 2016/0121128 A1 | 5/2016 | Fishler et al. |
| 2018/0035924 A1 | 1/2018 | Gunderson et al. |
| 2020/0086129 A1 | 3/2020 | Min et al. |
| 2021/0330986 A1 | 10/2021 | Min et al. |

OTHER PUBLICATIONS

Response to Office Action dated Apr. 20, 2021, U.S. Appl. No. 16/171,080, filed Oct. 25, 2018.
Notice of Allowance dated May 18, 2021, U.S. Appl. No. 16/171,080, filed Oct. 25, 2018.
Non-final Office Action dated Oct. 26, 2022, U.S. Appl. No. 17/370,210, filed Jul. 8, 2021.
Response to Office Action dated Jan. 18, 2023, U.S. Appl. No. 17/370,210, filed Jul. 8, 2021.
Notice of Allowance dated Feb. 8, 2023, U.S. Appl. No. 17/370,210, filed Jul. 8, 2021.
U.S. Appl. No. 18/162,226, filed Jan. 31, 2023.
Non-final Office Action dated Dec. 5, 2023, U.S. Appl. No. 18/162,226, filed Jan. 31, 2023.
Response to Office Action dated Feb. 13, 2024, U.S. Appl. No. 18/162,226, filed Jan. 31, 2023.
Notice of Allowance dated Feb. 28, 2024, U.S. Appl. No. 18/162,226, filed Jan. 31, 2023.

ENHANCED IMPLANT-TO-IMPLANT COMMUNICATIONS USING ACCELEROMETER

PRIORITY CLAIM

This application is a continuation of U.S. patent application Ser. No. 17/370,210, filed Jul. 8, 2021, issued as U.S. Pat. No. 11,642,536 on May 9, 2023, which is a continuation of U.S. patent application Ser. No. 16/171,080, filed Oct. 25, 2018, issued as U.S. Pat. No. 11,090,497 on Aug. 17, 2021, which claims priority to U.S. Provisional Patent Application No. 62/731,317, filed Sep. 14, 2018. Priority is claimed to each of the above applications, and each of the above applications is incorporated herein by reference.

RELATED APPLICATION

This application is related to U.S. patent application Ser. No. 18/162,226, filed Jan. 31, 2023, published as U.S. Publication No. 2023/0173284 on Jun. 8, 2023, which is incorporated herein by reference.

FIELD OF TECHNOLOGY

Embodiments described herein generally relate to methods and systems for communication between implantable medical devices, such as, but not limited to, leadless pacemakers.

BACKGROUND

Some medical systems rely on wireless communication between multiple implantable medical devices (IMDs). For example, in certain cardiac pacing systems, multiple IMDs wirelessly communicate with one another to reliably and safely coordinate pacing and/or sensing operations. Such a system may include, for example, one or more leadless pacemakers (LPs), an implantable cardioverter-defibrillator (ICD), such as a subcutaneous-ICD, and/or a programmer. For a more specific example, certain such systems include an LP in the right ventricle (RV) and another LP in the right atrium (RA), wherein the LPs in the RV and RA wirelessly communicate with one another to coordinate pacing and/or sensing operations. Such wireless communication between two IMDs (e.g., two LPs) is often referred to as implant-to-implant (i2i) communication.

When using a pair of LPs to perform pacing and/or sensing operations in the RA and RV, one of the challenges is that i2i communication is relied upon to maintain appropriate synchrony between the RA and the RV. However, it has been observed that such i2i communication can be adversely affected by the orientation of the LPs relative to one another.

SUMMARY

Embodiments of the present technology relate to implantable medical devices (IMDs) and methods for use therewith. A method according to an embodiment of the present is for use with an IMD that includes one or more pulse generators and an accelerometer. The accelerometer is configured to selectively produce one or more accelerometer outputs indicative of an orientation of the IMD. The one or more pulse generators is/are configured to selectively produce stimulation pulses and communication pulses. Such stimulation pulses are for use in pacing a cardiac chamber or performing neuromodulation. Such communication pulses are for use in performing conductive communication with another IMD or a non-implanted device.

In accordance with certain embodiments, the method includes using the accelerometer to produce one or more accelerometer outputs indicative of the orientation of the IMD. The method also includes controlling at least one communication pulse parameter of one or more communication pulses produced by at least one of the one or more pulse generators, wherein the controlling is based on at least one of the one or more accelerator outputs indicative of the orientation of the IMD. The at least one communication pulse parameter, that is controlled based on at least one of the one or more accelerator outputs indicative of the orientation of the IMD, can comprise, e.g., communication pulse amplitude, communication pulse width, communication pulse timing, and/or communication pulse morphology.

In accordance with certain embodiments, the IMD comprises a leadless pacemaker (LP) configured to be implanted in a cardiac chamber. In certain such embodiments the one or more accelerometer outputs is/are indicative of the orientation of the LP, the stimulation pulses are for use in pacing the cardiac chamber within which the LP is implanted, and the one or more communication pulses are for use in performing conductive communication with another LP. For example, one of the LPs can be implanted in the right atrium (RA), while the other LP is implanted in the right ventricle (RV), thereby enabling biventricular pacing to be performed. The one or more accelerometer outputs can be used to determine, e.g., the orientation of the LP relative to gravity, the orientation of the LP relative to an orientation of the other LP, and/or a posture of a patient within which the LP is implanted.

In accordance with certain embodiments, at least one communication pulse parameter is controlled, based on at least one of the one or more accelerator outputs indicative of the orientation of the LP, so that one or more communication pulses having a specified communication pulse amplitude is/are temporally produced so that a sense amplitude of one or more communication pulses received by the other LP will exceed a sense threshold. Additionally, at least one communication pulse parameter can be controlled, based on at least one of the one or more accelerator outputs indicative of the orientation of the LP, so that one or more communication pulses is/are temporally produced during a refractory period of the cardiac chamber within which the LP is implanted.

Additionally, or alternatively, at least one communication pulse parameter is controlled, based on at least one of the one or more accelerator outputs indicative of the orientation of the LP, so that a sense amplitude of one or more communication pulses received by the other LP will exceed a sense threshold. This can include, e.g., increasing at least one of the communication pulse amplitude or the communication pulse width in response to predicting that without the increasing one or more communication pulses received by the other LP will be below a sense threshold. In accordance with certain embodiments, in order to conserve power, at least one of the communication pulse amplitude or the communication pulse width is reduced in response to predicting that even with the reducing communication pulses received by the other LP will exceed a sense threshold.

Each of the LPs can include a plurality of electrodes that can be used for transmitting and receiving communication pulses. In accordance with certain embodiments, one of the LPs controls, based on at least one of the one or more accelerator outputs indicative of the orientation of the one of the LPs, which electrodes, of the plurality of electrodes of one of the LPs, are used to transmit or receive communication pulses to or from the other one of the LPs.

An IMD, according to certain embodiments of the present technology, includes one or more pulse generators, an accelerometer, and a controller. The accelerometer is configured to selectively produce one or more accelerometer outputs indicative of an orientation of the IMD. The controller, which is communicatively coupled to the accelerometer and to the one or more pulse generators, is configured to control at least one communication pulse parameter of one or more communication pulses produced by at least one of the one or more pulse generators, based on at least one of the one or more accelerator outputs indicative of the orientation of the IMD. The at least one communication pulse parameter, that the controller controls (based on at least one of the one or more accelerator outputs indicative of the orientation of the IMD) can comprise, e.g., communication pulse amplitude, communication pulse width, communication pulse timing, and/or communication pulse morphology.

An implantable system, according to an embodiment of the present technology, includes a first LP implanted within an atrial chamber, and a second LP implanted within a ventricular chamber. Each of the first and second LPs including one or more pulse generators configured to selectively produce stimulation pulses and communication pulses, the stimulation pulses for use in pacing the cardiac chamber within which the LP is implanted, and the communication pulses for use in performing conductive communication with the other LP. The first LP includes an accelerometer configured to selectively produce one or more accelerometer outputs indicative of an orientation of the first LP. The first LP also including a controller communicatively coupled to the accelerometer and to the one or more pulse generators of the first LP. The controller of the first LP is configured to control at least one communication pulse parameter of one or more communication pulses produced by at least one of the one or more pulse generators of the first LP, based on at least one of the one or more accelerator outputs indicative of the orientation of the first LP. Similarly, the second LP can include an accelerometer configured to selectively produce one or more accelerometer outputs indicative of an orientation of the second LP. The second LP can further include a controller communicatively coupled to the accelerometer and to the one or more pulse generators of the second LP. The controller of the second LP can be configured to control at least one communication pulse parameter (examples of which were mentioned above) of one or more communication pulses produced by at least one of the one or more pulse generators of the second LP, based on at least one of the one or more accelerator outputs indicative of the orientation of the second LP.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology relate to implantable systems, and methods for use therewith, that use one or more outputs of an accelerometer to improve conductive communications between multiple implantable medical device (IMDs) or between a non-implantable programmer and an IMD.

Before providing addition details of the specific embodiments of the present technology mentioned above, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more leadless pacemakers (LPs), an implantable cardioverter-defibrillator (ICD), such as a subcutaneous-ICD, and/or a programmer reliably and safely coordinate pacing and/or sensing operations.

Figure 1A:
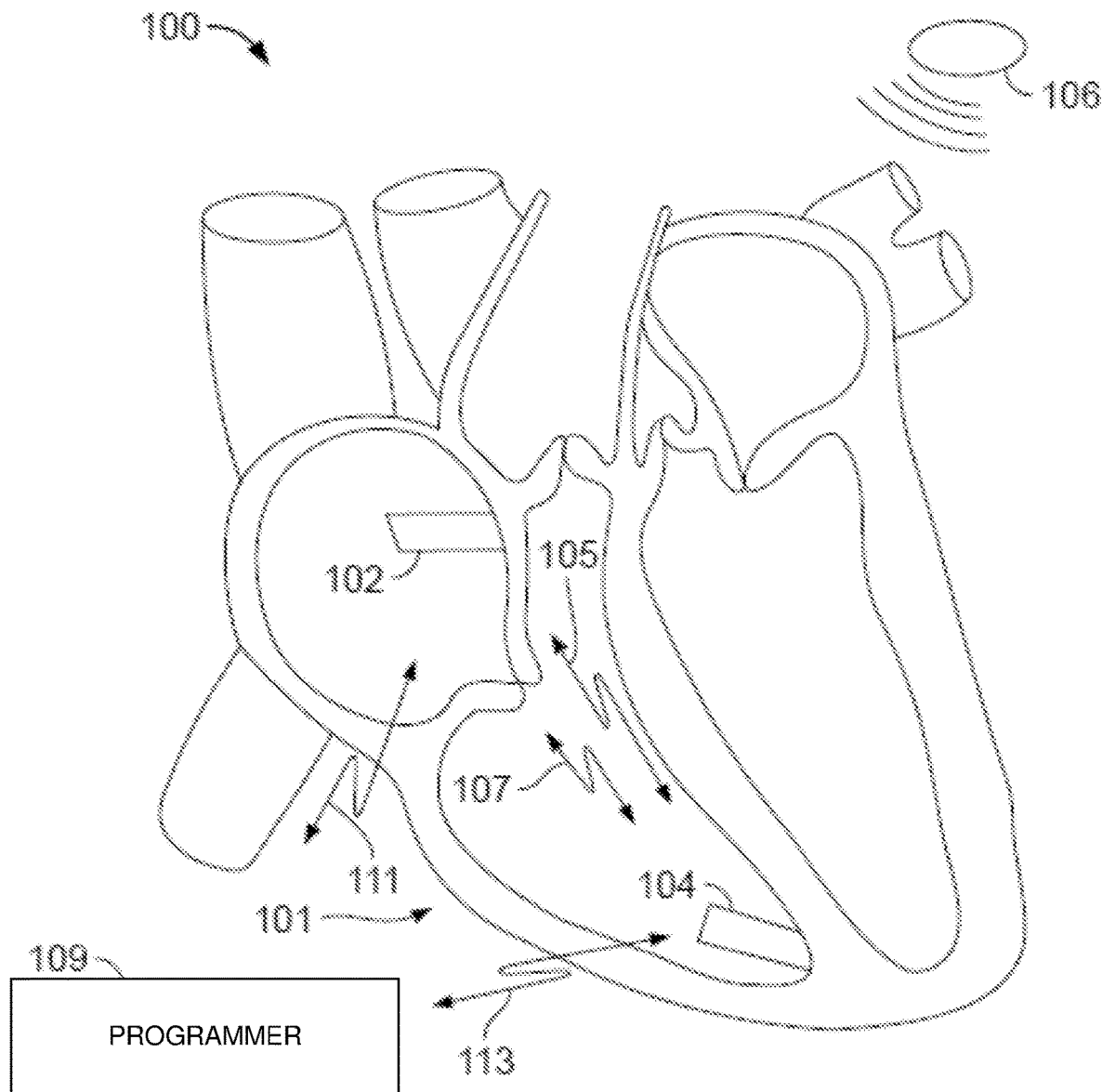
FIG. 1A illustrates a system formed in accordance with certain embodiments described herein as implanted in a heart.

FIG. 1A illustrates a system 100 formed in accordance with certain embodiments herein as implanted in a heart 101. The system 100 comprises two or more leadless pacemakers (LPs) 102 and 104 located in different chambers of the heart. LP 102 is located in a right atrium (RA), while LP 104 is located in a right ventricle (RV). The RA is also known as the right atrial chamber, and the RV is also known as the right ventricular chamber. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more LPs 102 and 104 can be co-implanted with the implantable cardioverter-defibrillator (ICD) 106. Each LP 102, 104 uses two or more electrodes located within, on, or within a few centimeters of the housing of the LP, for pacing and sensing at the cardiac chamber, for bidirectional communication with one another, with the programmer 109, and the ICD 106.

In accordance with certain embodiments, methods are provided for coordinating operation between LPs located in different chambers of the heart. The methods can configure a local LP to receive communications from a remote LP through conductive communication. While the methods and systems described herein include examples primarily in the context of LPs, it is understood that the methods and systems herein may be utilized with various other external and implanted devices. By way of example, the methods and systems may coordinate operation between various other types implantable medical devices (IMDs) implanted in a human, not just LPs.

Figure 1B:
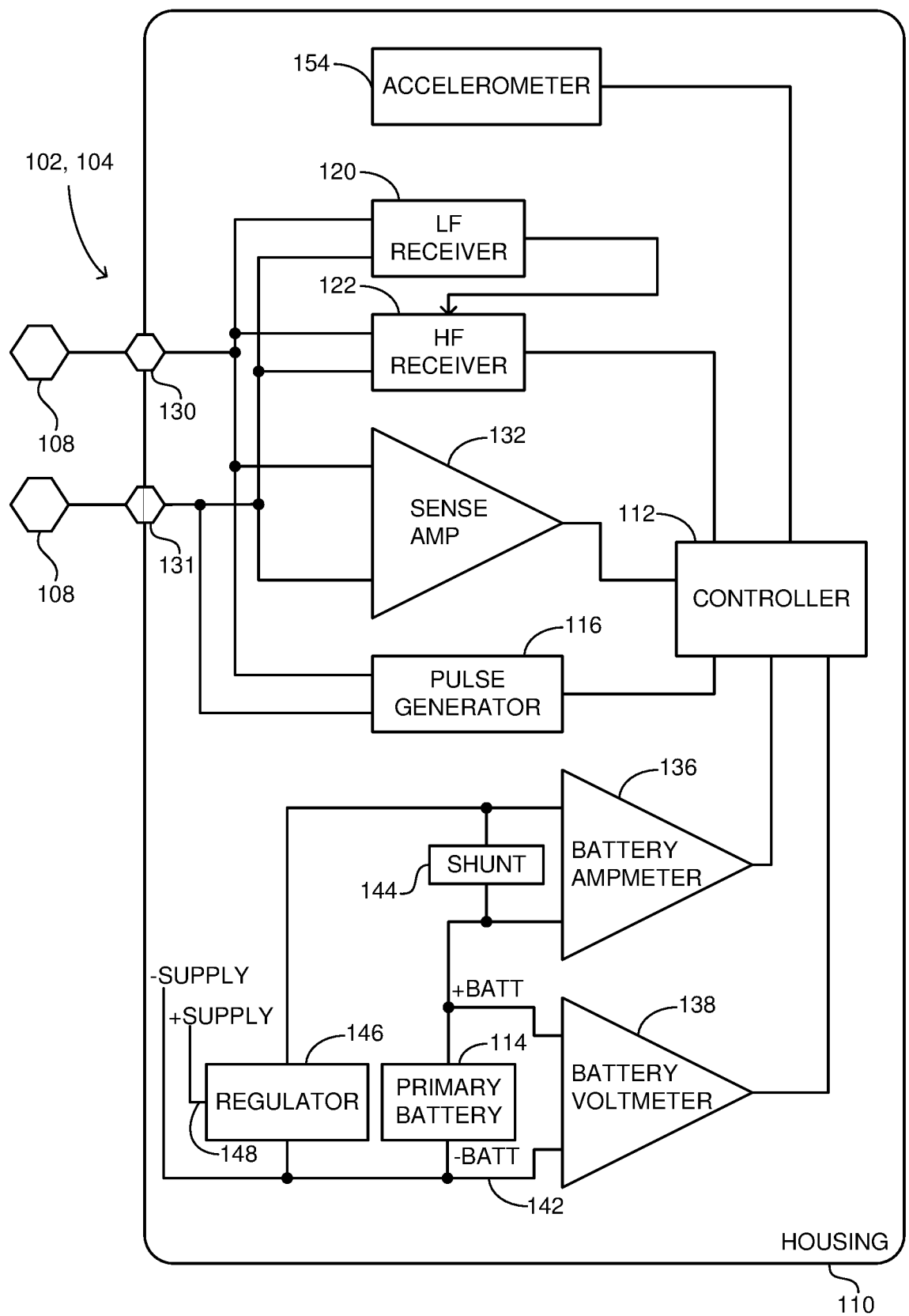
FIG. 1B is a block diagram of a single leadless pacemaker (LP) in accordance with certain embodiments herein.

Referring to FIG. 1B, a block diagram shows exemplary electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, the programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102, 104 may implement an event message utilizing event signaling parameters for amplitude, pulse-width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250nC (nano Coulombs) for an electrode load of 500 ohm. The pulses of the transmit event message may be followed by an event message encoded with a sequence of short duration pulses (for example 16, 2 µs on/off bits) which would draw an additional 80nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

Referring to FIG. 1B, the LP 102 (or 104) is shown as including an accelerometer 154 which can be hermetically contained within the housing 110. The accelerometer 154 can be any one of various different types of well known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Massachusetts) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for the accelerometer 154 to be a beam-type of accelerometer, an example of which is described in U.S. Pat. No. 6,252,335 (Nilsson et al.), which is incorporated herein by reference.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of $g \approx 9.81$ m/s^2.

Where an IMD (e.g., LP 102 or 104) includes an accelerometer within a housing of the IMD or attached thereto, the accelerometer can be used to measure the acceleration of the IMD along one or more axes, which measurement(s) can be used to determine the orientation of the IMD. Accordingly, because the output(s) of the accelerometer can be used to determine the orientation of the IMD, it can be said that the output(s) of the accelerometer (e.g., 154) are indicative of an orientation of the IMD (e.g., LP 102 or 104). More specifically, in accordance with certain embodiments, the controller 112 of an LP 102 (or 104) receives one or more outputs output(s) of the accelerometer 154, which is/are indicative of an orientation of the LP 102 (or 104). In such embodiments, the controller 112 can determine, based on the output(s) received from the accelerometer 154, an actual orientation of the LP 102 (or 104). Each output of the accelerometer 154 can comprise a respective signal.

One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, for sensing motion, for sensing temperature, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102, 104 and/or the ICD 106 and transmit data including designated codes for events detected or created by an individual LP. Individual LPs can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to LPs 102, 104 configured for implantation in electrical contact with a cardiac chamber and for performing cardiac rhythm management functions in combination with the implantable ICD 106. The implantable ICD 106 and the one or more LPs 102, 104 can be configured for leadless intercommunication by information conduction through body tissue and/or wireless transmission between transmitters and receivers in accordance with the discussed herein. As mentioned above, the ICD 106 can include its own motion sensor and/or temperature sensor.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, or one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACap-Confirm, sensing sensitivities, etc.).

Also shown in FIG. 1B, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102, 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102, 104 can be used to sense an intracardiac electrocardiogram (IEGM) from which atrial and/or ventricular activity can be detected, e.g., by detecting QRS complexes and/or P waves. Such an IEGM can also be used by an LP 102, 104 to time when communication pulses should be generated, since the orientation of the LPs 102, 104 relative to one another can change throughout each cardiac cycle.

Figure 2:
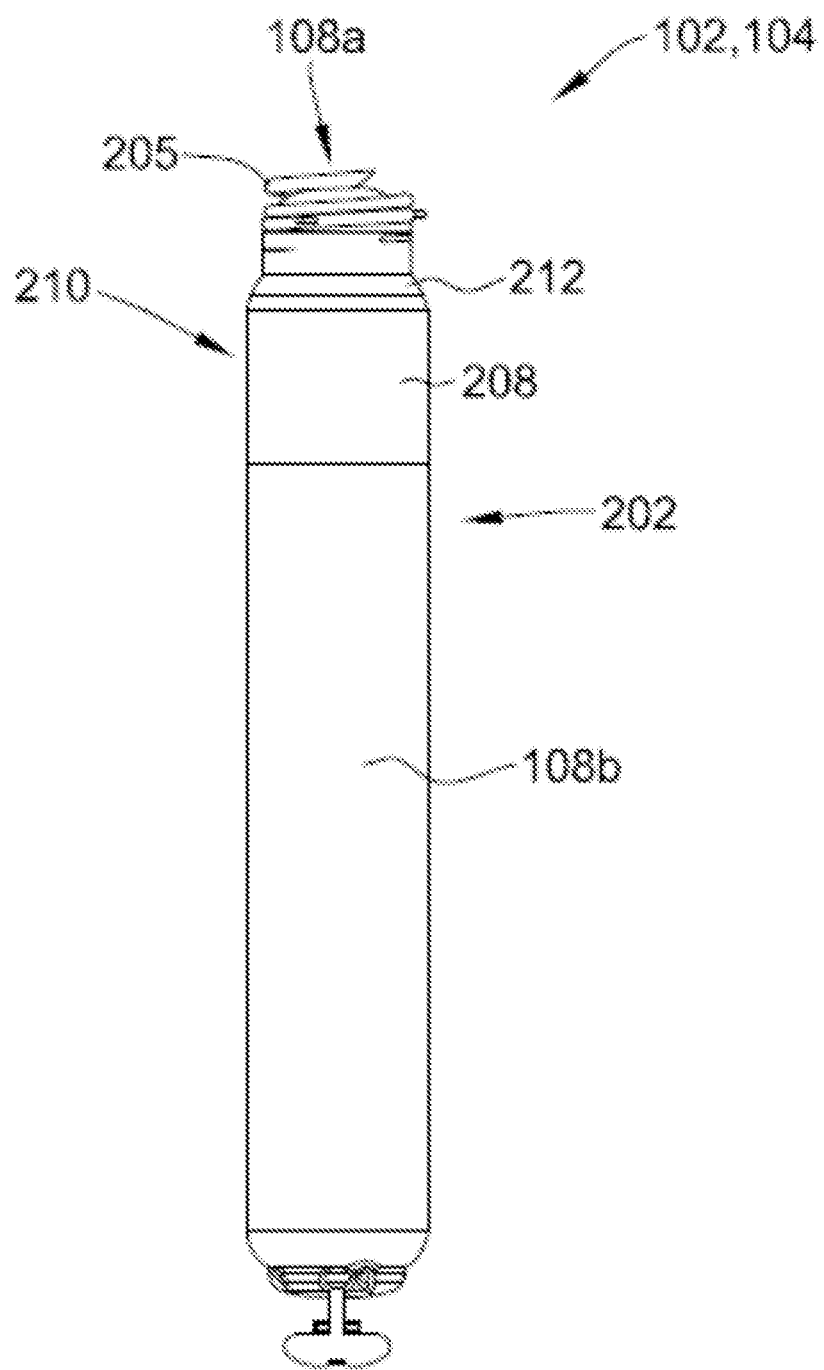
FIG. 2 illustrates an LP in accordance with certain embodiments herein.

FIG. 2 shows an LP 102, 104. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation.

The housing 202 can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 3:
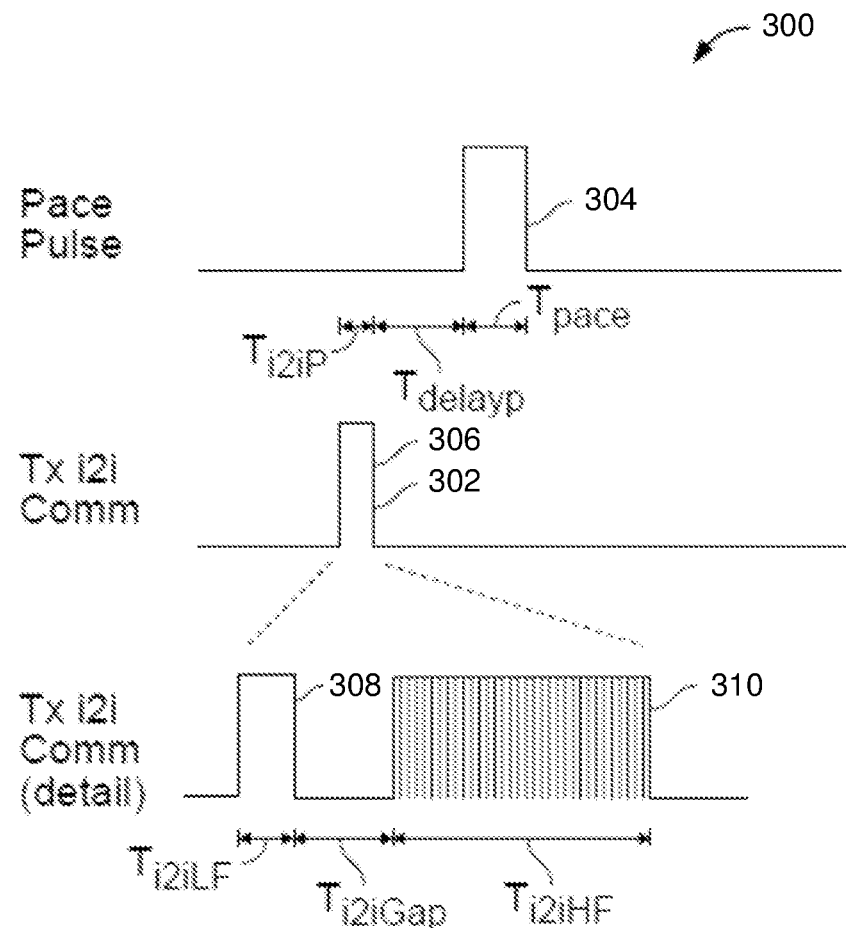
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from LP 102 to LP 104. As shown in FIG. 3, in this embodiment, an i2i transmission 302 is sent prior to delivery of a pace pulse 304 by the transmitting LP (e.g., LP 102). This enables the receiving LP (e.g., LP 104) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period Ti2iLF, and high frequency pulse train 310 lasts for a period Ti2iHF. The end of low frequency pulse 308 and the beginning of high frequency pulse train 310 are separated by a gap period, Ti2iGap.

As shown in FIG. 3, the i2i transmission 302 lasts for a period Ti2iP, and pace pulse 304 lasts for a period Tpace. The end of i2i transmission 302 and the beginning of pace pulse 304 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 4:
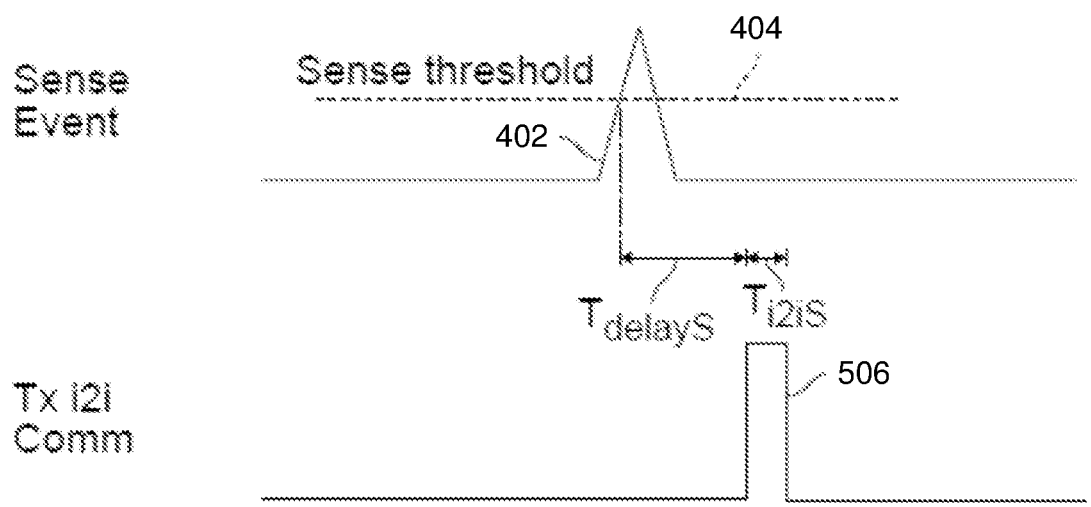
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from LP 102 to LP 104. As shown in FIG. 4, in this embodiment, the transmitting LP (e.g., LP 102) detects the sensed event when a sensed intrinsic activation 402 crosses a sense threshold 404. A predetermined delay period, $T_{delayS}$, after the detection, the transmitting LP transmits an i2i transmission 406 that lasts a predetermined period TIM. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 406, the envelope of i2i transmission 406 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
| --- | --- | --- |
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
| --- | --- | --- |
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

Enhanced i2i Communication Using Accelerometer

As noted above, when using a pair of LPs (e.g., 102, 104) to perform pacing and/or sensing operations in the RA and RV, one of the challenges is that i2i communication is relied upon to maintain appropriate synchrony between the RV and the RA.

As also noted above, a transmitter (e.g., 118) of an LP 102, 104 may be configured to transmit event messages in a manner that does not inadvertently capture the heart in the chamber where LP 102, 104 is located, such as when the associated chamber is not in a refractory state. In addition, an LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104. The amplitude of a detected (i.e., sensed) measurement pulse can be referred to as the sensed amplitude.

As noted above, it has been observed that i2i communication can be adversely affected by the orientation of the LPs relative to one another. Both computer simulations and animal testing have showed that sensed amplitude varied widely with different orientation angles. For example, where a first LP (e.g., 102) transmits a pulse having a pulse amplitude of 2.5V to a second LP (e.g., 104), the sensed amplitude of the pulse received by the second LP (e.g., 104) could vary from about 2 mV to less than 0.5 mV, depending upon the orientation between the first and second LPs (e.g., 102 and 104). For example, where the LP 102 is implanted in the right atrium (RA), and the LP 104 is implanted in the left atrium (LA), e.g., as shown in FIG. 1A, the orientation of the LPs 102 and 104 relative to one another can change over the course of each cardiac cycle. Additionally, the orientation of the LPs 102 and 104 relative to one another can be affected by the posture of the patient. Accordingly, since the sensed amplitude of a pulse received by one LP (e.g., 104) from the other LP (e.g., 102) can significantly vary based on the orientation of the LPs relative to one another, the sense amplitude can significantly vary depending upon the timing of when a pulse is transmitted during a cardiac cycle, as well as the posture of the patient when the pulse is transmitted.

Assume, for example, that an LP 102, 104 has a 0.5 mV sense threshold, meaning that a sensed pulse must have an amplitude of at least 0.5 mV in order to be detected as a communication pulse by the receiving LP. In other words, if sensed amplitudes of received communication pulses are below the sense threshold, the receiving LP will fail to receive the information encoded therein and may fail to respond accordingly, which is undesirable.

Figure 5:
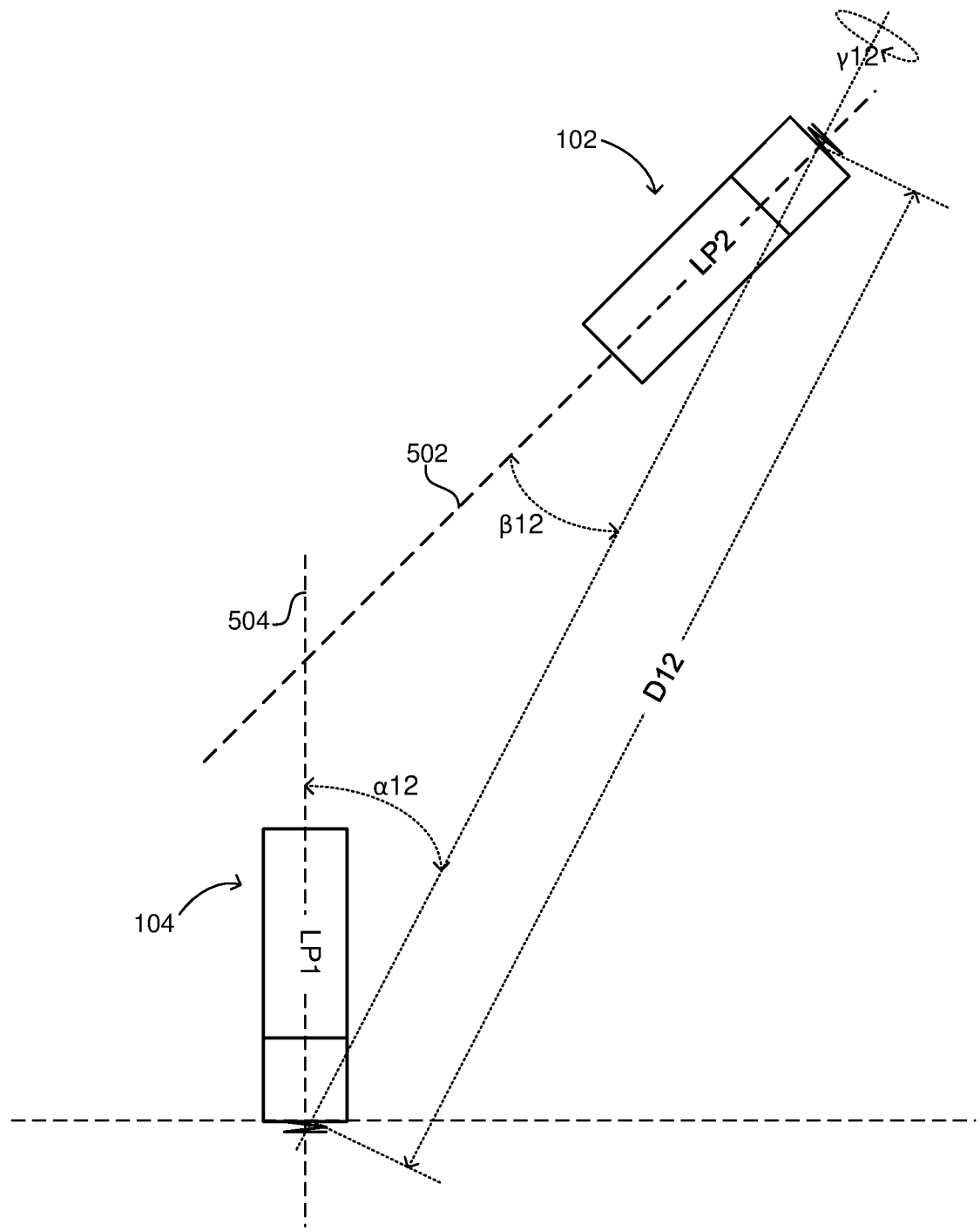
FIG. 5 is a diagram that is used to show how the orientation of two different LPs can be quantified in accordance with certain embodiments of the present technology.
Figure 6:
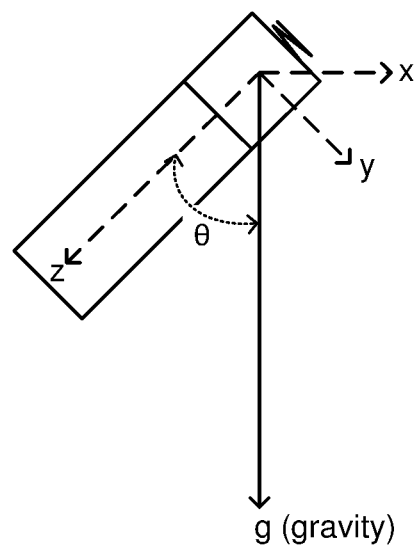
FIG. 6 is used to illustrates how an LP and/or external programmer can convert local coordinate system measurements to global coordinate measurements in accordance with certain embodiments of the present technology.

FIG. 5 is a diagram that is used to show how the orientation of two different LPs (e.g., 102, 104), labeled LP2 and LP1 in FIG. 5, can be quantified. Referring to FIG. 5, the LP2 (e.g., 102) is shown as having an axis 502, and the LP1 (e.g., 104) is shown as having an axis 504. The line D12 represents the distance between the LP1 and the LP2. In FIG. 5, the angle $\alpha 12$ is the angle between the axis 504 of the LP1 and the line D12; the angle $\beta 12$ is the angle between the axis 502 of the LP2 and the line D12; and the angle $\gamma 12$ is angle between the plane defined by the angle $\alpha 12$ and the plane defined by the angle $\beta 12$.

Table 3, below, provides the results of simulations that show how sensed amplitudes are affected by the orientation of LP1 and LP2 relative to one another, where the LP2 is assumed to be implanted in the RA, the LP1 is assumed to be implanted in the RV, and the distance D12 is assumed to be fixed at 125 millimeters (mm).

TABLE 3

| Distance D12 | Angle $\alpha 12$ | Angle $\beta 12$ | RA → RV | RA ← RV |
|---|---|---|---|---|
| 124 mm | 20° | 12° | 2.5 V → 2.13 mV | 2.11 mV ← 2.5 V |
| 124 mm | 20° | 32° | 2.5 V → 1.82 mV | N/A |
| 124 mm | 20° | 52° | 2.5 V → 1.32 mV | N/A |
| 124 mm | 20° | 72° | 2.5 V → 0.745 mV | N/A |
| 124 mm | 20° | 82° | 2.5 V → 0.470 mV | 0.460 mV ← 2.5 V |
| 124 mm | 20° | 92° | 2.5 V → 0.198 mV | 0.198 mV ← 2.5 V |
| 124 mm | 10° | 82° | 2.5 V → 0.6627 mV | N/A |
| 124 mm | 40° | 82° | 2.5 V → −0.1135 mV | N/A |
| 124 mm | 50° | 82° | N/A | N/A |

The first row of Table 3 shows that when the angle $\beta 12$ (i.e., the angle between the axis 502 of the LP2 and the line D12) is 12 degrees, in response to the LP2 transmitting a communication pulse having an amplitude of 2.5V, the sense amplitude of the communication pulse received by the LP1 will be 2.13 mV, which is well above a 0.5 mV sense threshold. By contrast, the sixth row of Table 3 shows that when the angle $\beta 12$ is 92 degrees, in response to the LP2 transmitting a communication pulse having an amplitude of 2.5V, the sense amplitude of the communication pulse received by the LP1 will be only 0.198 mV, which is well below the 0.5 mV sense threshold. Looking at the right most column and the first row of Table 3 shows that when the angle $\beta 12$ is 12 degrees, in response to the LP1 transmitting a communication pulse having an amplitude of 2.5V, the sense amplitude of the communication pulse received by the LP2 will be 2.11 mV, which is well above a 0.5 mV sense threshold; and when the angle β12 is 92 degrees, in response to the LP1 transmitting a communication pulse having an amplitude of 2.5V, the sense amplitude of the communication pulse received by the LP2 will be only 0.198 mV, which is well below the 0.5 mV sense threshold.

With larger heart sizes, the sensed amplitudes decrease. More specifically, a larger heart can cause the distance D12 between the LP1 and the LP2 to increase, with the results summarized in Table 4, below.

TABLE 4

| Distance D12 | Angle α12 | Angle β12 | RA → RV | RA ← RV |
|---|---|---|---|---|
| 150 mm | 20° | 12° | 2.5 V → 0.96 mV | N/A |
| 150 mm | 20° | 32° | 2.5 V → 0.76 mV | N/A |
| 150 mm | 20° | 52° | 2.5 V → 0.51 mV | N/A |
| 150 mm | 20° | 72° | 2.5 V → 0.25 mV | N/A |
| 150 mm | 20° | 82° | 2.5 V → 0.12 mV | N/A |
| 150 mm | 20° | 92° | 2.5 V → 0.005 mV | N/A |
| 150 mm | 20° | 52° | 2.5 V → 0.51 mV | N/A |
| 150 mm | 10° | 52° | 2.5 V → 0.59 mV | N/A |
| 150 mm | 40° | 52° | 2.5V → 0.27 mV | N/A |

The results summarized in Table 4 mimic a worst case where the heart size is at the upper bounds (D12~150 mm). As can be appreciated from a comparison between Table 4 and Table 3, the sensed amplitudes decreased as D12 was increased from 124 mm to 150 mm, so that in Table 4 when the angle β12 is greater than 52 degree, the sensed amplitude is lower than the 0.5 mV sense threshold. Accordingly, it can be appreciated that i2i communications between LPs implanted in larger hearts are even more adversely affected than smaller hearts by the relative orientation of the LPs.

When performing i2i communication, the one or more pulses that are transmitted from one LP to another LP can be referred more generally as the i2i signal. Due to the nature of electrode potential distribution, bipolar sensing of the i2i signal (by the LP that is receiving/sensing the i2i signal) is minimal along iso-potential lines and maximum along lines orthogonal to the iso-potential lines. In other words, when the respective axes (e.g., 502 and 504 in FIG. 5) of the two LPs (communicating with one another) are aligned with one another the sensed i2i signal is near its maximum, and when the respective axes (e.g., 502 and 504 in FIG. 5) of the two LPs are orthogonal to one another the sensed i2i signal is near its minimum.

For the purpose of this discussion, when LPs are oriented relative to another such that (for a give transmitted communication pulse amplitude) the sense amplitude of the communication pulse received by an LP will be below the sense threshold (e.g., 0.5 mV), the LPs can be said to be within a "deaf zone". This is because under such circumstances the LPs cannot successfully communicate or "hear" one another even though they are attempting to communicate or "talk" with one another.

Certain embodiments of the present technology utilize one or more accelerometers to time the sending and/or receiving of communication pulses during time windows when the LPs (or other types of IMDs) are not within a deaf zone, or more generally, when the LPs (or other types of IMDs) have an acceptable alignment or orientation. In other words, in accordance with certain embodiments, communication pulse timing is controlled based on one or more accelerator outputs. Alternatively, or additionally, one or more accelerometers can be used to control one or more other types of communication pulse parameters besides communication pulse timing. For example, in accordance with certain embodiments, communication pulse amplitude and/or width may be increased when LPs (or other types of IMDs) are within or close to a deaf zone to improve the chance that a sense amplitude exceeds a sense threshold. Additionally, or alternatively, it would also be possible to modify a communication pulse morphology based on one or more accelerometer outputs. For example, a decision to transmit either biphasic or monophasic communication pulses can depend upon one or more accelerometer outputs. For example, in accordance with certain embodiments, communication pulse morphology can be changed from a first morphology (e.g., monophasic) to a second morphology (e.g., biphasic) when LPs (or other types of IMDs) are within or close to a deaf zone to improve the chance that a sense amplitude exceeds a sense threshold. Further, in certain embodiments communication pulse amplitude and/or width may be decreased when it is determined that LPs (or other types of IMDs) are oriented relative to one another such that sense amplitudes will be at or close to maximum (e.g., when respective axes of two LPs are aligned or close to aligned). More generally, in accordance with certain embodiments of the present technology, at least one communication pulse parameter of one or more communication pulses (produced by at least one of one or more pulse generators, e.g., 116 in FIG. 2B) is/are controlled based on one or more outputs of one or more accelerometers (e.g., 154 in FIG. 2B).

Within this description, phrases such as "the orientation of two LPs (or other type of IMDs) relative to one another" are used synonymously with phrases such as "the orientation of one LP (or other type of IMD) relative to another LP (or other IMD)". In accordance with certain embodiments of the present technology, the orientation of two LPs (or other type of IMDs) relative to one another is taken into account to control at least one communication pulse parameter (e.g., pulse amplitude, pulse width, pulse timing, and/or pulse morphology) in order to improve the probability that communication from one of the LPs (or other type of IMD) to the other is successful, and more specifically, exceeds a sense threshold.

One possible way that an LP (or other type of IMD) can determine whether it is at an acceptable orientation relative to another LP (or other type of IMD) is by receiving orientation information from the other LP. However, this would not practical where the whole purpose of a first LP obtaining the orientation information from a second LP is to determine whether and/or how the first LP should communicate with the second LP. To overcome this problem, in accordance with certain embodiments of the present technology, an initialization process is performed which, at later times, enables a first LP (or other type of IMD) to determine a likely orientation relative to a second LP (or other type of IMD) based on the first LP's own orientation, a posture of a patient within which the LPs are implanted, and/or cardiac cycle timing.

In accordance with certain embodiments, an initialization process can take place (e.g., in a physician's or clinician's office) while the two LPs (or other types of IMDs) are in communication with an external programmer, at the same time, or one after the other. Alternatively, each of the LPs (or other types of IMDs) can go through an initialization routine, save its results, and upload the saved results to an external program (e.g., 109 in FIG. 1A).

During an initialization period, for each of a plurality of different postures (e.g., supine, sitting, and standing, but not limited thereto), accelerometer data can be obtained for each LP, and such data can be used to determine the relative orientation of two LPs over the course of a cardiac cycle for each of the plurality of different postures. Based on such accelerometer data, a respective table can be generated for each LP (or other type of IMD) by the external programmer and then downloaded to the LPs (or other types of IMDs). Such tables enable each individual LP to determine a likely orientation of the other LP based on its own orientation (or more generally, its own acceleration output(s)), a posture of the patient (as determined based on its own acceleration output(s)), and/or timing within a cardiac cycle (as determined based on an IEGM obtained using electrodes of the LP). The timing within a cardiac cycle is likely important because the orientation of an LP can vary over each cardiac cycle, e.g., as the cardiac chamber within which (or to which) the LP is attached expands and contracts. Based on such a table, an LP can determine when it is acceptable to send one or more communication pulses to another LP at a baseline communication pulse amplitude and width. Additionally, or alternatively, the LP can determine when it should delay sending the communication pulse(s), and/or increase the communication pulse amplitude and/or width, and/or modify the communication pulse morphology, in order to increase a probability that when the communication pulse(s) is/are received by the other LP the sense threshold is exceeded (thereby enabling the other LP to successfully receive and interpret the communication pulse(s)).

Figure 7:
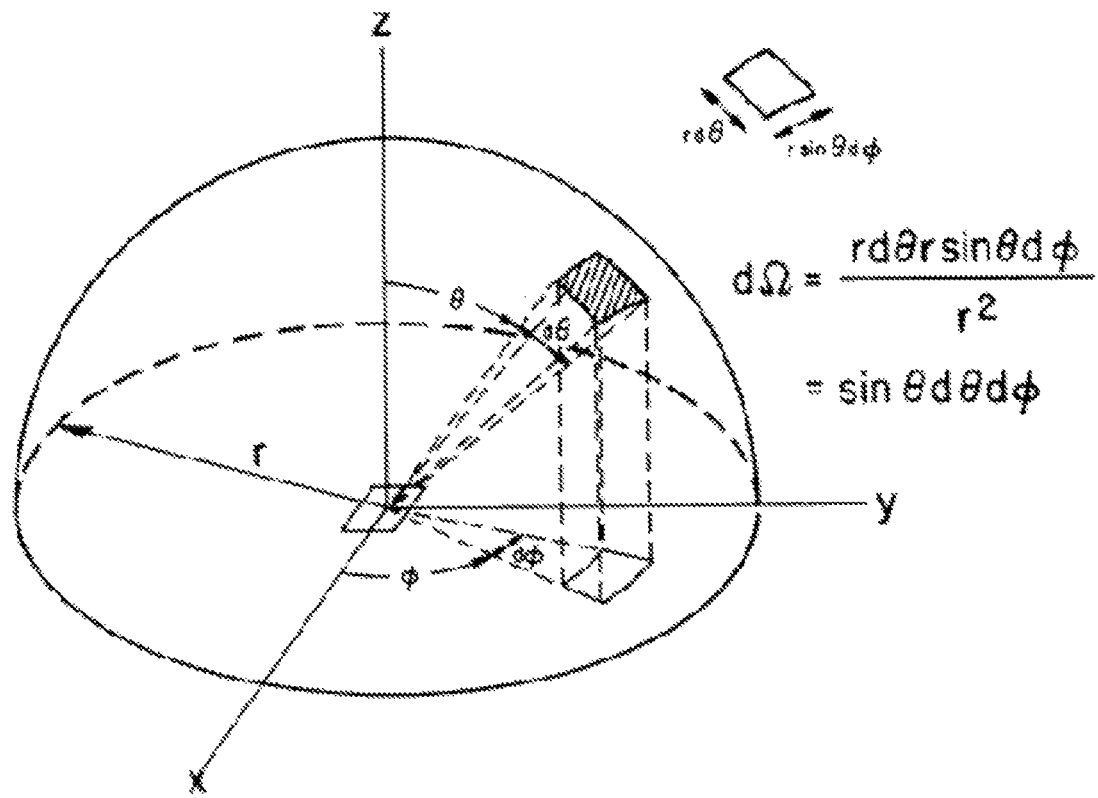
FIG. 7 includes a diagram and equations that illustrate one exemplary manner in which a local coordinate system can be converted to a global coordinate system.

In accordance with certain embodiments, the orientation of each LP (or other type of IMD) can be determined within a global coordinate system defined by or relative to gravity. For example, each LP can determine its own orientation based on three outputs of its own 3D accelerometer, and such measures can be translated into the global coordinate system defined by or relative to gravity. This way multiple LPs (or other types of IMDs) can utilize a common coordinate system, i.e., the global coordinate system. For a more specific example, each LP can determine its own values of $\theta$ and $\varphi$, based on outputs of its respective accelerometer and using a calibration process, and such values can be used to derive values for the angles $\alpha 12$ and $\beta 12$, discussed above with reference to FIG. 5 and Tables 3 and 4. Such a calibration process may be performed, e.g., during one or more office visits, during which a global z axis can be determined while a patient is standing, a global x axis can extend from arm to arm of the patient, and a global y axis would be orthogonal to the global z and x axes. With the global axes defined, values of $\theta$ and $\varphi$ can be determined. The diagram and equations shown in FIG. 7 illustrate one exemplary way that a local coordinate system can be converted to a global coordinate system. In the present case, the variable r=gravity g, and the solid angle $d\Omega$ can be used to define each posture associated with the local coordinate angles $\theta$ and $\varphi$. Other variations are possible and within the embodiments of the present technology described herein.

Where the accelerometer 154 of an LP (or other type of IMD) is a 3D accelerometer, the accelerometer can produce three outputs, one of which is indicative of acceleration in the x-direction, one of which is indicative of acceleration in the y-direction, and one of which is indicative of acceleration in the z-direction. Each of these three outputs can be, e.g., a DC signal having a magnitude that is proportional to acceleration in a specific direction. It is also possible that each of these three outputs can be a digital value indicative of acceleration in a specific direction. Regardless of the format of the outputs, the outputs can correspond to a local coordinate system of the IMD within which the accelerometer is located. For example, the three outputs of the accelerometer of the LP1 can be referred to as x1, y1, and z1; and the three outputs of the accelerometer of the LP2 can be referred to as x2, y2, and z2. In accordance with certain embodiments, gravity g can be used as a global reference that enables a determination of the orientation of LP1 and LP2 relative to one another. For example, this can be accomplished by mathematically projecting gravity g to the 3D accelerometer outputs produced by LP1 to produce gx1, gy1, gz1, and by LP2 to produce gx2, gy2, gz2.

Depending upon implementation, e.g., including the specific tables stored in the LPs, an LP can determine whether it (and/or another LP) is likely in a deaf zone based on outputs of its own accelerometer (e.g., 154) as well as cardiac cycle timing as determined based on an IEGM obtaining using its own electrodes (e.g., 108). As already noted above, an LP has a few options when it determines that it (and/or another LP) is likely in a deaf zone. The LP can increase its communication pulse amplitude and/or communication pulse width. Alternatively, or additionally, the LP can delay sending one or more communication pulse(s) until it (and/or the other LP) is no longer within a deaf zone. In accordance with certain embodiments, the amount of the delay, which can be referred to as the delta ($\Delta$), should be less than an absolute refractory period (~200 ms). Additionally, where communication pulse(s) is/are being sent from an LP within an atrium (e.g., the RA) to an LP within a ventricle (e.g., the RV), the amount of the delay (i.e., $\Delta$) should also be less than a programmed AV delay, especially when the communication pulse(s) is/are being used to inform the LP within the RV of a sensed or paced event in the RA.

In certain embodiments, if a first LP predicts (based on its own orientation and the likely orientation of a second LP) that pulses the first LP sends to the second LP (using a baseline amplitude and pulse width) will be received below, but close, to the sense threshold (e.g., will be slightly less than 0.5 mV), then the first LP can determine that it should increase its pulse amplitude and/or pulse width when sending communication pulse(s) to the second LP. However, if the first LP predicts that pulses it sends to the second LP will be received significantly below the sense threshold (e.g., will be much less than 0.5 mV), then the first LP can decide to delay sending the pulses until the relative orientation of the LPs is more acceptable.

In accordance with certain embodiments, whenever a first LP delays sending communication pulse(s) to a second LP, the first LP informs the second LP of the amount of communication delay. That way the second LP will known if it needs to adjust certain timed events based on the communication delay. For an example, assume a first LP located in the RA sends communication pulses to a second LP in order to inform the second LP of a sensed or paced even in the RA. Also assume that the second LP is programmed to pace the RV at in accordance with predetermined AV delay of 220 ms. If the first LP send communication pulses to the second LP immediately upon pacing or sensing an atrial even, then the second LP can simply trigger delivery of the RV pacing 220 ms (i.e., the AV delay) after receiving the communication pulses from the first LP (potentially minus some time it is presumed for the communication to occur). However, if the first LP didn't send its communication pulses to the second LP until some delay (e.g., 50 ms) after pacing or sensing an atrial even, then the second LP would need to know of and compensate for such a delay, e.g., by triggering delivery of the RV pacing based on the AV delay minus the communication delay (and potentially minus some time it is presumed for the communication to occur). In accordance with certain embodiments, certain bits of a communication packet sent from the first LP to the second LP can be designated for specifying such a communication delay. Other variations are also possible and within the scope of embodiments of the present technology described herein.

A potential problem with an LP relying on its accelerometer to determine its orientation is that the LP will be unable to determine its orientation when it is orthogonal to gravity (g). When an LP (e.g., LP1) determines from its accelerometer that it is orthogonal to gravity (g), then that LP (e.g., LP1) cannot determine its own orientation, and thus, cannot determine (e.g., from a table and/or algorithm) the orientation of another LP (e.g., LP2) with which the LP (e.g., LP1) wants to communicate. Thus, when an LP determines that it is orthogonal to gravity, that LP cannot determine whether itself and/or another LP is likely in a deaf zone. To overcome this problem, the LP can wait until it is no longer orthogonal to gravity (e.g., because its own orientation changed due to cardiac motion) to determine its own orientation and/or the orientation of another LP. This is another example of when an LP may delay sending one or more communication pulse(s) to another LP. Once the LP is no longer orthogonal to gravity, and can determine its own orientation, the LP can also determine the orientation of another LP, in a manner described above, to know if it should further delay sending communication pulse(s) and/or adjust the amplitude of communication pulse(s).

As noted above, in certain embodiments, one LP may act as a "master" device, while another LP acts as a "slave" device. For example, as explained above, where there are two LPs, with one in an atrium and the other in a ventricle, the vLP can act as the "master" device, while the aLP acts as the "slave" device. In certain such embodiments, the slave LP can send its accelerometer data (alone, or together with other data, such as atrial activity data) to the master LP via conductive i2i communications, and the master LP can use its own accelerometer data and the accelerometer data received from the slave LP to calculate θ and φ for both LPs to determine when they may be in or close to the "deaf zone". More generally, in certain embodiments a master LP can determine the orientation of itself based on its own accelerometer data and determine the orientation of the slave LP based on accelerometer data received from the slave LP. This should work fine so long as the slave LP does not try to send its accelerometer data to the master LP via conductive i2i communications when the master LP is in the deaf zone. One way to overcome this potential problem is for the slave LP to keep resending its accelerometer data (alone, or together with other data, such as atrial activity data) via conductive i2i communications to the master LP until the slave LP receives a reception acknowledgement back from the master LP. The resent i2i communication pulses can be sent at a delay after to the initial i2i communications pulses, to try to take advantage of the likelihood that the orientation of the LPs relative to one another may have changed (e.g., due to cardiac motion), and thus, that they are no longer in the deaf zone. Additionally, or alternatively, the resent i2i communication pulses can be sent at an increased amplitude, increasing the probability that when received at the master LP they will exceed the sense threshold. If accelerometer data is resent along with other data, such as atrial activity data, at a delayed time relative to when it was initially sent, the slave LP can inform the master LP of the time delay so that the master LP can determine, e.g., an actual time of atrial activity, or the like.

While in many examples described above, the communication pulses were described as being used for performing conductive communications between LPs, embodiments of the present technology can also be used to improve conductive communications between other types of IMDs (besides LPs), as well as to improve conductive communications between an IMD (e.g., an LP or ICD) and a non-implanted device (e.g., an external programmer). Further, while in many examples described above the IMDs (e.g., LPs or ICD) were described as being used to deliver cardiac stimulation (e.g., for pacing or defibrillation), it is also possible that one or more of the IMDs be used to deliver neurostimulation, such as, but not limited to, spinal cord stimulation (SCS), dorsal root ganglion (DRG) stimulation, brain stimulation, deep brain stimulation, and/or the like. In other words, IMDs that implement embodiments of the present technology can alternatively be (or include) a neurostimulator that, similar to an LP or ICD, also included one or more pulse generators that produce stimulation pulses and communication pulses.

Figure 8A:
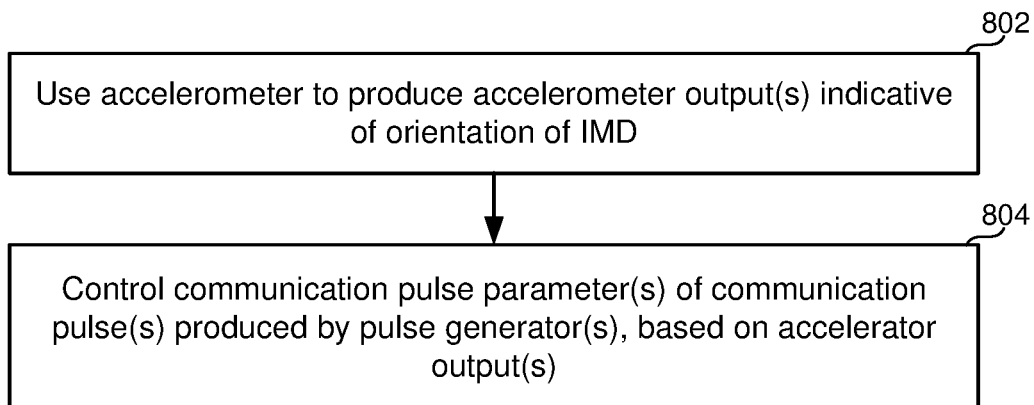
FIGS. 8A and 8B are a high level flow diagrams that are used to summarize methods according to various embodiments of the present technology that can be used to improve or otherwise control conductive communications.

The high level flow diagram of FIG. 8A will be now be used to summarize methods for use with an IMD that includes one or more pulse generators and an accelerometer, wherein the accelerometer is configured to selectively produce one or more accelerometer outputs indicative of an orientation of the IMD, and the one or more pulse generators is/are configured to selectively produce stimulation pulses and communication pulses. The stimulation pulses can be used for pacing a cardiac chamber. The stimulation pulses can alternatively be used for performing neuromodulation. The communication pulses are for use in performing conductive communication with another IMD or a non-implanted device.

Referring to FIG. 8A, step 802 involves using the accelerometer to produce one or more accelerometer outputs indicative of the orientation of the IMD. Referring briefly back to FIG. 1B, step 802 can be performed, e.g., using the accelerometer 154 under the control of the controller 112.

Referring again to FIG. 8A, step 804 involves controlling at least one communication pulse parameter of one or more communication pulses produced by at least one of the one or more pulse generators, wherein the controlling is based on at least one of the one or more accelerator outputs indicative of the orientation of the IMD. Referring briefly back to FIG. 1B again, step 804 can be performed, e.g., using the controller 112 and the pulse generator 116.

The communication pulse parameter(s), that is/are controlled at step 804 (based on at least one of the one or more accelerator outputs indicative of the orientation of the IMD) can be one or more of communication pulse amplitude, communication pulse width, communication pulse timing, or communication pulse morphology.

As can be appreciated from the above discussion of FIGS. 1-7, in certain embodiments, the IMD with which the methods summarized with reference to FIG. 8A can be used, can be an LP (e.g., 102 and/or 104) configured to be implanted in a cardiac chamber, e.g., the RA or RV. In such embodiments, the accelerometer output(s) can be indicative of the orientation of the LP, and more specifically, can be indicative of the orientation of the LP relative to gravity, indicative of the orientation of the LP relative to an orientation of the other LP, and/or indicative of a posture of a patient within which the LP is implanted. Additionally, in such embodiments, the stimulation pulses can be for use in pacing the cardiac chamber within which the LP is implanted, and the communication pulses can be for use in performing conductive communication with another LP. As can be appreciated from the above discussion of FIGS. 1A, 1B and 2, such an LP can include electrodes (e.g., 108) that can be used for transmitting and receiving communication pulses, as well as for sensing and delivering cardiac stimulation.

In accordance with certain embodiments, step 804 involves controlling the communication pulse timing so that one or more communication pulses having a specified communication pulse amplitude is/are temporally produced so that a sense amplitude of one or more communication pulses received by the other LP will exceed a sense threshold (e.g., 0.5 mV).

In accordance with certain embodiments, step 804 involves controlling the communication pulse timing so that one or more communication pulses is/are temporally produced during a refractory period of the cardiac chamber within which the LP is implanted.

In accordance with certain embodiments, step 804 involves controlling the communication pulse amplitude and/or the communication pulse width so that a sense amplitude of one or more communication pulses received by the other LP will exceed a sense threshold. For example, this can include increasing the communication pulse amplitude and/or the communication pulse width in response to predicting that without such increasing communication pulses received by the other LP will be below the sense threshold.

In accordance with certain embodiments, step 804 involves reducing the communication pulse amplitude and/or the communication pulse width in response to predicting that even with the reducing communication pulses received by the other LP will exceed a sense threshold. Such embodiments can be used to conserve power, and thus, increase the longevity of the IMD that is implementing such a method.

In still other embodiments, accelerator output(s) can be used to guide, or at least help guide, an auto-adjusting of the sense threshold. Additionally, or alternatively, accelerator output(s) can be used to "steer" i2i communications in order to limit effects on nearby devices not intended to detect a particular communication.

Figure 8B:
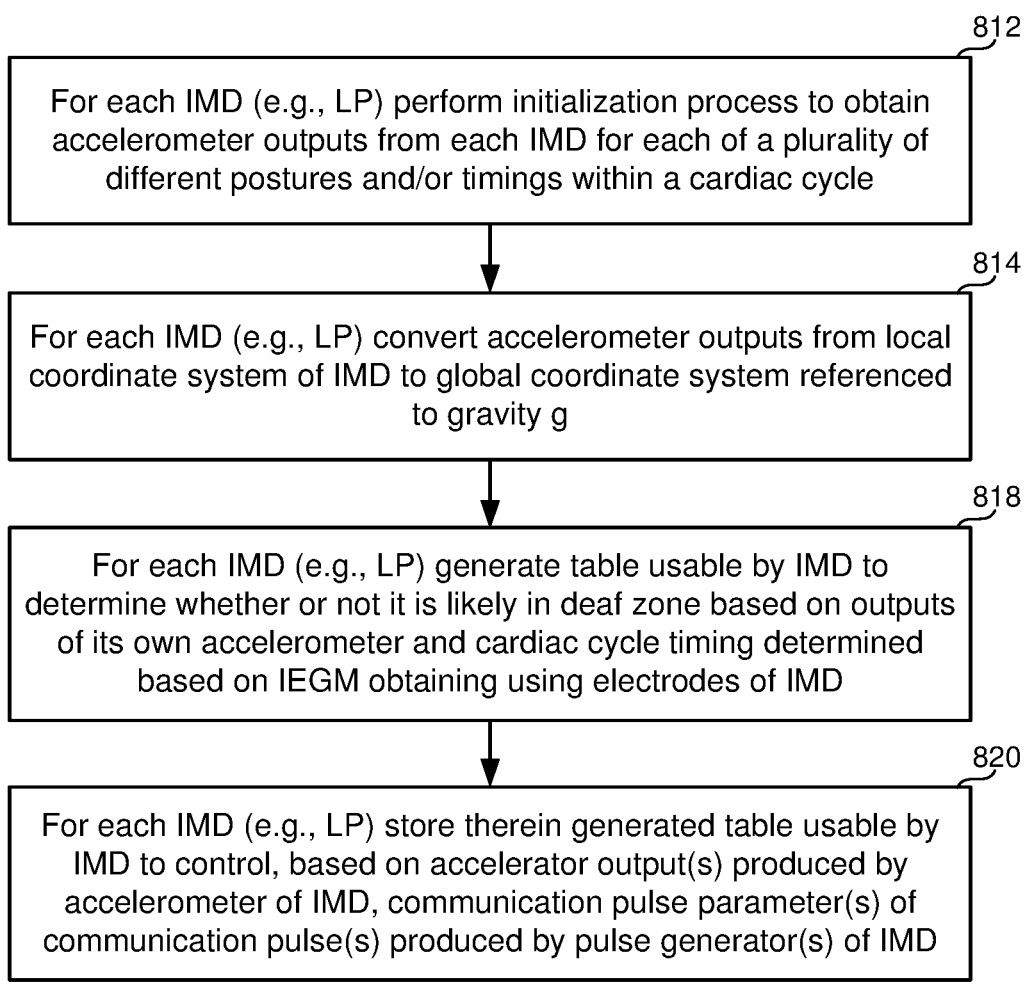

The high level flow diagram of FIG. 8B will now be used to summarize further features of the embodiments described herein. Referring to FIG. 8B, step 812 involves for each IMD (e.g., LP) performing an initialization process in order to obtain accelerometer outputs from each IMD for each of a plurality of different postures and/or times within a cardiac cycle.

Step 814 involves, for each IMD (e.g., LP), converting accelerometer outputs from a local coordinate system of the IMD to a global coordinate system referenced to gravity g.

Step 816 involves, for each IMD (e.g., LP), generating a table that can be used by the IMD to determine whether or not it is likely in a deaf zone based on outputs of its own accelerometer as well as cardiac cycle timing as determined based on an IEGM obtaining using its own electrodes.

Step 818 involves, for each IMD (e.g., LP), storing within the IMD (e.g., in the IMD's memory) the table that has been generated for the IMD, so that the table can be used by the IMD to control communication pulse parameter(s) of communication pulse(s) produced by pulse generator(s) of the IMD, based on accelerator output(s) produced by the accelerometer of the IMD.

In the exemplary LP 102, 104 described above with reference to FIGS. 1A, 1B and 2, the LP was shown as and described as having a pair of electrodes 108 (e.g., labeled 108*a* and 108*b* in FIG. 2). As was mentioned above, one of the electrodes 108 (e.g., 108*a*) can function as a cathode type electrode and another one of the electrodes 108 (e.g., 108*b*) can function as an anode type electrode, or vice versa, when the electrodes are used for delivering stimulation. In FIG. 2, the electrode 108*b* is shown as being a ring electrode that extends around an entire circumference of a portion of the LP 102, 104. In alternative embodiments, the electrode 108*b* can be a slit ring electrode, meaning the electrode 108*b* can be capable of being electrically separated into halves of some other portions (e.g., thirds, fourths, etc.), depending upon design. For example, if split into halves, each half can take up 180 degrees of a 360 degree ring; or if slit into quarters, each quarter can take up 90 degrees of a 360 degree ring. By changing which one or more portion(s) of the electrode 108*b* is/are used for sensing (or transmitting) communication pulses, the sense vector (or transmission vector) can be adjusted to improve conductive communication in dependence on the relative orientation of two LPs (or other types of IMDs) as determined based on accelerometer outputs. More generally, in accordance with certain embodiments, electrode sensing and/or transmitting vectors can be adjusted based on one or more accelerometer outputs to improve conductive communications.

Figure 9:
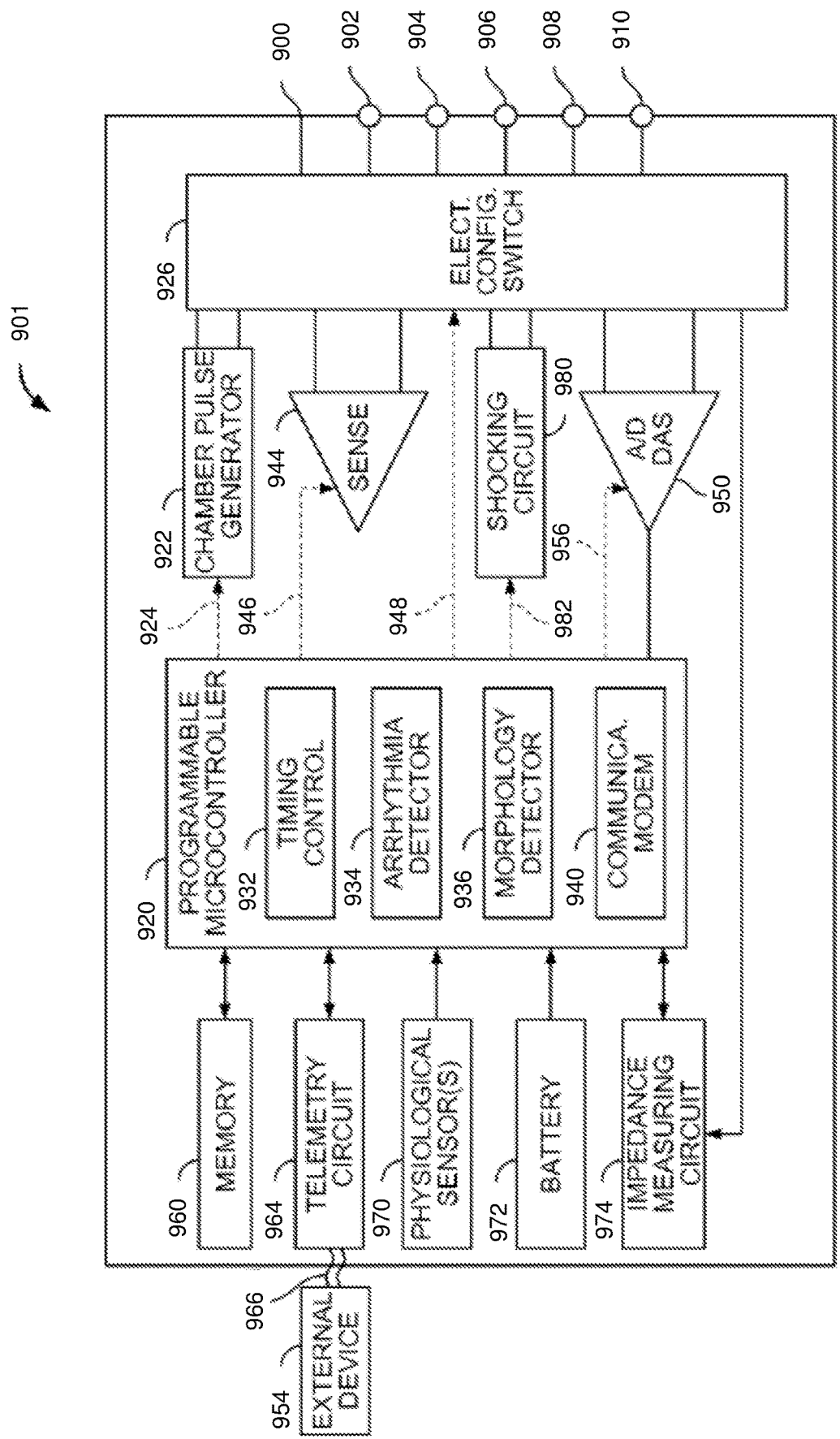
FIG. 9 shows a block diagram of one embodiment of an LP that is implanted into a patient as part of an implantable cardiac system in accordance with certain embodiments herein.

FIG. 9 shows a block diagram of one embodiment of an LP 901 that is implanted into the patient as part of the implantable cardiac system in accordance with certain embodiments herein. LP 901 may be implemented as a full-function biventricular pacemaker, equipped with both atrial and ventricular sensing and pacing circuitry for four chamber sensing and stimulation therapy (including both pacing and shock treatment). Optionally, LP 901 may provide full-function cardiac resynchronization therapy. Alternatively, LP 901 may be implemented with a reduced set of functions and components. For instance, the IMD may be implemented without ventricular sensing and pacing.

LP 901 has a housing 900 to hold the electronic/computing components. Housing 900 (which is often referred to as the "can", "case", "encasing", or "case electrode") may be programmably selected to act as the return electrode for certain stimulus modes. Housing 900 may further include a connector (not shown) with a plurality of terminals 902, 904, 906, 908, and 910. The terminals may be connected to electrodes that are located in various locations on housing 900 or elsewhere within and about the heart. LP 901 includes a programmable microcontroller 920 that controls various operations of LP 901, including cardiac monitoring and stimulation therapy. Microcontroller 920 includes a microprocessor (or equivalent control circuitry), RAM and/or ROM memory, logic and timing circuitry, state machine circuitry, and I/O circuitry.

LP 901 further includes a pulse generator 922 that generates stimulation pulses and communication pulses for delivery by one or more electrodes coupled thereto. Pulse generator 922 is controlled by microcontroller 920 via control signal 924. Pulse generator 922 may be coupled to the select electrode(s) via an electrode configuration switch 926, which includes multiple switches for connecting the desired electrodes to the appropriate I/O circuits, thereby facilitating electrode programmability. Switch 926 is controlled by a control signal 928 from microcontroller 920.

In the embodiment of FIG. 9, a single pulse generator 922 is illustrated. Optionally, the IMD may include multiple pulse generators, similar to pulse generator 922, where each pulse generator is coupled to one or more electrodes and controlled by microcontroller 920 to deliver select stimulus pulse(s) to the corresponding one or more electrodes.

Microcontroller 920 is illustrated as including timing control circuitry 932 to control the timing of the stimulation pulses (e.g., pacing rate, atrio-ventricular (AV) delay, atrial interconduction (A-A) delay, or ventricular interconduction (V-V) delay, etc.). Timing control circuitry 932 may also be used for the timing of refractory periods, blanking intervals, noise detection windows, evoked response windows, alert intervals, marker channel timing, and so on. Microcontroller 920 also has an arrhythmia detector 934 for detecting arrhythmia conditions and a morphology detector 936. Although not shown, the microcontroller 920 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

LP 901 is further equipped with a communication modem (modulator/demodulator) 940 to enable wireless communication with the remote slave pacing unit. Modem 940 may include one or more transmitters and two or more receivers as discussed herein in connection with FIG. 1B. In one implementation, modem 940 may use low or high frequency modulation. As one example, modem 940 may transmit i2i messages and other signals through conductive communication between a pair of electrodes. Modem 940 may be implemented in hardware as part of microcontroller 920, or as software/firmware instructions programmed into and executed by microcontroller 920. Alternatively, modem 940 may reside separately from the microcontroller as a standalone component.

LP 901 includes a sensing circuit 944 selectively coupled to one or more electrodes, that perform sensing operations, through switch 926 to detect the presence of cardiac activity in the right chambers of the heart. Sensing circuit 944 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 926 determines the sensing polarity of the cardiac signal by selectively closing the appropriate switches. In this way, the clinician may program the sensing polarity independent of the stimulation polarity.

The output of sensing circuit 944 is connected to microcontroller 920 which, in turn, triggers or inhibits the pulse generator 922 in response to the presence or absence of cardiac activity. Sensing circuit 944 receives a control signal 946 from microcontroller 920 for purposes of controlling the gain, threshold, polarization charge removal circuitry (not shown), and the timing of any blocking circuitry (not shown) coupled to the inputs of the sensing circuitry.

In the embodiment of FIG. 9, a single sensing circuit 944 is illustrated. Optionally, the IMD may include multiple sensing circuits, similar to sensing circuit 944, where each sensing circuit is coupled to one or more electrodes and controlled by microcontroller 920 to sense electrical activity detected at the corresponding one or more electrodes. Sensing circuit 944 may operate in a unipolar sensing configuration or in a bipolar sensing configuration.

LP 901 further includes an analog-to-digital (A/D) data acquisition system (DAS) 950 coupled to one or more electrodes via switch 926 to sample cardiac signals across any pair of desired electrodes. Data acquisition system 950 is configured to acquire intracardiac electrogram signals, convert the raw analog data into digital data, and store the digital data for later processing and/or telemetric transmission to an external device 954 (e.g., a programmer, local transceiver, or a diagnostic system analyzer). Data acquisition system 950 is controlled by a control signal 956 from the microcontroller 920.

Microcontroller 920 is coupled to a memory 960 by a suitable data/address bus. The programmable operating parameters used by microcontroller 920 are stored in memory 960 and used to customize the operation of LP 901 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 901 may be non-invasively programmed into memory 960 through a telemetry circuit 964 in telemetric communication via communication link 966 with external device 954. Telemetry circuit 964 allows intracardiac electrograms and status information relating to the operation of LP 901 (as contained in microcontroller 920 or memory 960) to be sent to external device 954 through communication link 966.

LP 901 can further include magnet detection circuitry (not shown), coupled to microcontroller 920, to detect when a magnet is placed over the unit. A magnet may be used by a clinician to perform various test functions of LP 901 and/or to signal microcontroller 920 that external device 954 is in place to receive or transmit data to microcontroller 920 through telemetry circuits 964.

LP 901 can further include one or more physiological sensors 970. Such sensors are commonly referred to as "rate-responsive" sensors because they are typically used to adjust pacing stimulation rates according to the exercise state of the patient. However, physiological sensor 970 may further be used to detect changes in cardiac output, changes in the physiological condition of the heart, or diurnal changes in activity (e.g., detecting sleep and wake states). Signals generated by physiological sensors 970 are passed to microcontroller 920 for analysis. Microcontroller 920 responds by adjusting the various pacing parameters (such as rate, AV Delay, V-V Delay, etc.) at which the atrial and ventricular pacing pulses are administered. While shown as being included within LP 901, physiological sensor(s) 970 may be external to LP 901, yet still be implanted within or carried by the patient. Examples of physiologic sensors might include sensors that, for example, sense respiration rate, pH of blood, ventricular gradient, activity, position/posture, minute ventilation (MV), and so forth.

A battery 972 provides operating power to all of the components in LP 901. Battery 972 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 972 also desirably has a predictable discharge characteristic so that elective replacement time can be detected. As one example, LP 901 employs lithium/silver vanadium oxide batteries.

LP 901 further includes an impedance measuring circuit 974, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 974 is coupled to switch 926 so that any desired electrode may be used. In this embodiment LP 901 further includes a shocking circuit 980 coupled to microcontroller 920 by a data/address bus 982.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in improving conductive communication can also be used with other types of IMDs besides an LP. Accordingly, unless specifically limited to use with an LP, the claims should not be limited to use with LP type IMDs. For example, embodiments of the present technology can also be used with a subcutaneous-ICD and/or a subcutaneous pacemaker, but are not limited thereto.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 8A and 8B. For another example, it is possible to change the boundaries of some of the dashed blocks shown in FIGS. 1B and 9.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use with an implantable medical device (IMD) that includes one or more pulse generators and an accelerometer, the accelerometer configured to produce one or more accelerometer outputs indicative of an orientation of the IMD, the one or more pulse generators configured to produce stimulation pulses and communication pulses, the stimulation pulses for use in pacing a cardiac chamber or performing neuromodulation, and the communication pulses for use in performing conductive communication with another IMD, the method comprising:

the IMD using the accelerometer to identify when the orientation of the IMD is such that the IMD will likely be able to successfully communicate with the other IMD via one or more communication pulses sent from the IMD to the other IMD; and the IMD sending of the one or more communication pulses, that are used to communicate with the other IMD, when the orientation of the IMD is such that the IMD will likely be able to successfully communicate with the other IMD via one or more communication pulses sent from the IMD to the other IMD.

2. The method of claim 1, wherein:
the IMD comprises a leadless pacemaker (LP) implanted in or on a first cardiac chamber.

3. The method of claim 2, wherein:
the other IMD comprises a second LP implanted in or on a second cardiac chamber.

4. The method of claim 3, wherein:
the first cardiac chamber comprises one of a left ventricular (LV) chamber and a right ventricular (RV) chamber; and
the second cardiac chamber comprises the other one of the LV chamber and the RV chamber.

5. The method of claim 2, wherein:
the other IMD comprises an implantable cardioverter-defibrillator (ICD).

6. The method of claim 5, wherein:
the ICD comprises a subcutaneous-ICD.

7. A method for use with an implantable medical device (IMD) that includes one or more pulse generators and an accelerometer, the accelerometer configured to produce one or more accelerometer outputs indicative of an orientation of the IMD, the one or more pulse generators configured to produce stimulation pulses and communication pulses, the stimulation pulses for use in pacing a cardiac chamber or performing neuromodulation, and the communication pulses for use in performing conductive communication with another IMD, the method comprising:
storing information that specifies when the orientation of the IMD is such that the IMD and the other IMD implanted in a patient are likely oriented relative to one another such that conductive communication between the IMD and the other IMD should be successful;
determining, based on at least one of the one or more accelerometer outputs, and the stored information, when the orientation of the IMD is such that the IMD and the other IMD implanted in the patient are likely oriented relative to one another such that conductive communication between the IMD and the other IMD should be successful; and
outputting one or more conductive communication pulses that are intended for reception by the other IMD, when the orientation of the IMD is such that the IMD and the other IMD implanted in the patient are likely oriented relative to one another such that conductive communication between the IMD and the other IMD should be successful.

8. The method of claim 7, wherein:
the IMD comprises a leadless pacemaker (LP) implanted in or on a first cardiac chamber.

9. The method of claim 8, wherein:
the other IMD comprises a second LP implanted in or on a second cardiac chamber.

10. The method of claim 9, wherein:
the first cardiac chamber comprises one of a left ventricular (LV) chamber and a right ventricular (RV) chamber; and
the second cardiac chamber comprises the other one of the LV chamber and the RV chamber.

11. The method of claim 7, wherein:
the other IMD comprises an implantable cardioverter-defibrillator (ICD).

12. The method of claim 11, wherein:
the ICD comprises a subcutaneous-ICD.

13. An implantable medical device (IMD), comprising:
one or more pulse generators configured to produce stimulation pulses and communication pulses, the stimulation pulses for use in pacing a cardiac chamber or performing neuromodulation, and the communication pulses for use in performing conductive communication with another IMD or a non-implanted device;
an accelerometer configured to produce one or more accelerometer outputs indicative of an orientation of the IMD; and
a controller communicatively coupled to the accelerometer and to the one or more pulse generators, the controller configured to
identify, based on at least one of the one or more accelerometer outputs, when the orientation of the IMD is such that the IMD will likely be able to successfully communicate with the other IMD via one or more communication pulses sent from the IMD to the other IMD; and
control at least one of the one or more pulse generators to output the one or more communication pulses, that are used to communicate with the other IMD, when the orientation of the IMD is such that the IMD will likely be able to successfully communicate with the other IMD via the one or more communication pulses sent from the IMD to the other IMD.

14. The IMD of claim 13, wherein:
the IMD comprises a leadless pacemaker (LP) configured to be implanted in or on a first cardiac chamber.

15. The IMD of claim 14, wherein:
the other IMD comprises a second LP configured to be implanted in or on a second cardiac chamber.

16. The IMD of claim 15, wherein:
the first cardiac chamber comprises one of a left ventricular (LV) chamber and a right ventricular (RV) chamber; and
the second cardiac chamber comprises the other one of the LV chamber and the RV chamber.

17. The IMD of claim 13, wherein:
the other IMD comprises an implantable cardioverter-defibrillator (ICD).

18. The IMD of claim 17, wherein:
the ICD comprises a subcutaneous-ICD.

19. An implantable medical device (IMD) configured to be implanted in a patient and to perform conductive communication with another IMD that is also configured to be implanted in the patient, the IMD comprising:
a plurality of electrodes;
an accelerometer configured to produce one or more accelerometer outputs indicative of an orientation of the IMD; and
memory that stores information that specifies when the orientation of the IMD is such that the IMD and the other IMD are likely oriented relative to one another such that conductive communication between the IMD and the other IMD should be successful;
one or more pulse generators coupled to at least two of the electrodes;
a controller communicatively coupled to the memory, the accelerometer, and the one or more pulse generators, the controller configured to:
determine, based on at least one of the one or more accelerometer outputs, and the stored information, when an orientation of the IMD is such that the IMD and the other IMD are likely oriented relative to one another such that conductive communication between the IMD and the other IMD should be successful; and
control at least one of the one or more pulse generators to output one or more conductive communication pulses that are intended for reception by the other IMD, when the orientation of the IMD is such that the IMD and the other IMD are likely oriented relative to one another such that conductive communication between the IMD and the other IMD should be successful.

20. The IMD of claim 19, wherein:
the IMD comprises a leadless pacemaker (LP) configured to be implanted in or on a first cardiac chamber.

21. The IMD of claim 20, wherein:
the other IMD comprises a second LP configured to be implanted in or on a second cardiac chamber.

22. The IMD of claim 21, wherein:
the first cardiac chamber comprises one of a left ventricular (LV) chamber and a right ventricular (RV) chamber; and
the second cardiac chamber comprises the other one of the LV chamber and the RV chamber.

23. The IMD of claim 20, wherein:
the other IMD comprises an implantable cardioverter-defibrillator (ICD).

24. The IMD of claim 23, wherein:
the ICD comprises a subcutaneous-ICD.

\* \* \* \* \*